US006151124A

United States Patent [19]

Visscher

[11] Patent Number: 6,151,124

[45] Date of Patent: Nov. 21, 2000

[54] INSPECTION SYSTEM

[76] Inventor: Paul R. Visscher, 6283 136th Ave., Saugatuck, Mich. 49453

[21] Appl. No.: 09/144,243

[22] Filed: Aug. 31, 1998

[51] Int. Cl.[7] .......... G01N 21/55

[52] U.S. Cl. .......... 356/445

[58] Field of Search .......... 356/445

[56] References Cited

FOREIGN PATENT DOCUMENTS 401192486 8/1989 Japan .

403297584 12/1991 Japan .

*Primary Examiner*—Frank G. Font

*Assistant Examiner*—Zandra V. Smith

*Attorney, Agent, or Firm*—Malcolm B. McKinnon

[57] ABSTRACT

An improved inspection system for verifying that resistance welding electrodes been properly dressed, the system incorporating novel fiber-optic sensors that evaluate the light-reflective characteristics of the surfaces of welding electrodes to determine such characteristics meet predetermined criteria.

12 Claims, 4 Drawing Sheets

INSPECTION SYSTEM

BRIEF SUMMARY OF THE INVENTION

This invention relates to inspection systems and, more particularly, to an improved inspection system for verifying that resistance welding electrodes have been properly dressed by an electrode tip dresser.

As is well known in the art, during resistance welding processes the tips of the electrodes tend to mushroom (flatten) due to the pressures applied by the weld gun and the electrical current that passes through the electrode tips. Also, for example, in the case of welding galvanized steel, a build-up of brass alloy will form on the surface of the electrode tips. Both of such conditions are causes of poor welds being produced. Consequently, the electrode tips must be dressed periodically to insure that the tip configuration is maintained within predetermined tolerances. As is also well known in the art, in automated welding systems the use of automatic electrode tip dressers has developed. Although the automated tip dressers are reliable there are cases in which the electrode tips are not properly dressed or are not dressed at all because of broken or dull dresser cutter blades or other factors. Electrode tips that are not properly dressed can also result in welds of poor quality, and in some cases no welds whatsoever are produced. Consequently, the resulting sub-standard parts can have various types of negative consequences, such as requiring the re-working of parts, added costs, necessity of parts-sorting, possible liability issues, poor customer relations and other adverse consequences.

It is well known in the art that the tips of standard alloy electrodes, which are lustrous and glistening, i.e. highly light reflective, when new and/or when properly dressed, become blackened and less light reflective during resistance welding processes. Moreover, improperly dressed electrodes tips do not exhibit the highly light reflective characteristics that are exhibited by properly dressed electrode tips.

An object of the present invention is to overcome the aforementioned problems which can be created when the tips of resistance welding electrodes are not properly dressed, and to provide an improved inspection system for verifying that resistance welding electrode tips have been properly dressed by an electrode tip dresser thereby reducing the risks involved in the spot welding of metal components and also reducing the problems that are caused by welding with electrodes having tips that are not properly dressed.

Another object of the present invention is to provide an improved inspection system incorporating novel fiber-optic sensing means for evaluating welding electrode tip faces, physical shape and condition, and the relationship of such tips to predetermine criteria.

Another object of the present invention is to provide an improved inspection system incorporating fiber-optic sensing means capable of simultaneously sensing two opposing electrode tips to evaluate the suitability thereof for continuing welding operations satisfying predetermined standards.

Another object of the present invention is to provide an improved inspection system embodying fiber-optic sensing means incorporating interchangeable collets permitting the inspection of welding electrodes of various sizes and shapes merely by interchanging the collets.

Another object of the present invention is to provide an improved inspection system that permits two welding electrodes of different sizes and shapes to be inspected at the same time.

A further object of the present invention is to provide an improved inspection system for verifying that the tips of welding electrodes have been properly dressed, and which system is capable of being mounted in close proximity to an electrode tip dresser machine and/or a welding gun.

Yet another object of the present invention is to provide an improved inspection system that is relatively easy to manufacture and assemble at economical cost while providing long life and reliability in operation.

The above as well as other objects and advantages of the present invention will become apparent from the following description, the appended claims, and the accompanying drawings.

DETAILED DESCRIPTION

Figure 1:
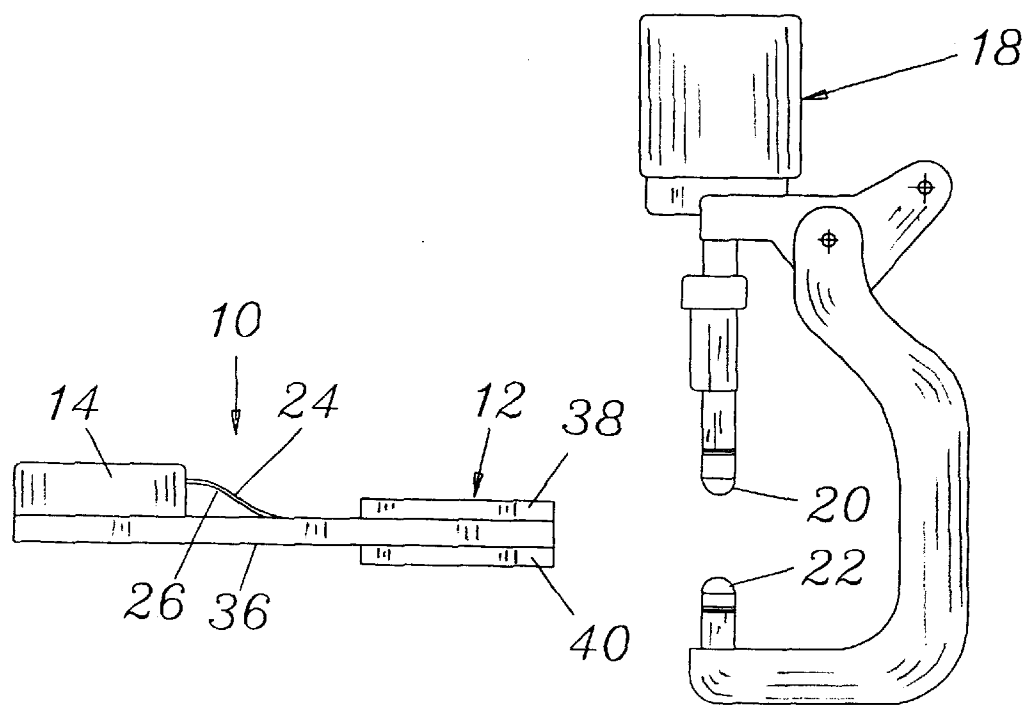
FIG. 1 is a schematic elevational view of an inspection system embodying the present invention, showing the same in relationship with respect to a welding gun having opposed welding electrodes.

Referring to the drawings, the present invention is illustrated as embodied in an inspection system, generally designated 10, which is particularly adapted for use in verifying that resistance welding electrodes have been properly dressed by an electrode tip dresser. It will be understood, however, that the present invention is applicable to other uses. The inspection system 10 is comprised of a sensor 12 which is fiber-optically connected to a pair of high precision combined light generating and reflected light sensing units 14 and 16. By way of example, the units 14 and 16 may be of the type commercially identified as "OMRON" Model E3X-NH high precision fiber-optic amplifiers available from Grand Technologies, Inc., Grand Rapids, Mich. 49512.

A conventional welding gun 18 is schematically illustrated in FIG. 1 of the drawings, the gun having an upper electrode 20 and a lower electrode 22 which cooperate to resistance weld workpieces disposed between the electrodes 20 and 22 in a conventional manner. In order to obtain good welds, the electrodes 20 and 22 must be properly dressed through the agency of an automatic electrode tip dresser (not shown) or other suitable dresser means. The inspection system 10 embodying the present invention may be mounted in close proximity to the welding gun 18, as illustrated in FIG. 1 of the drawings, or the inspection system 10 may be mounted on a dresser machine framework or on a separate pedestal (not shown) as desired.

The sensor 12 is fiber-optically connected to the units 14 and 16 by fiber cables 24 and 26 having side view heads 28 and 30, respectively. By way of example, the heads 28 and 30 may be of the type commercially identified as "OMROM" Model E32-D24 fiber-optic heads which are also available from Grand Technologies, Inc., Grand Rapids, Mich. 49512.

Figure 2:
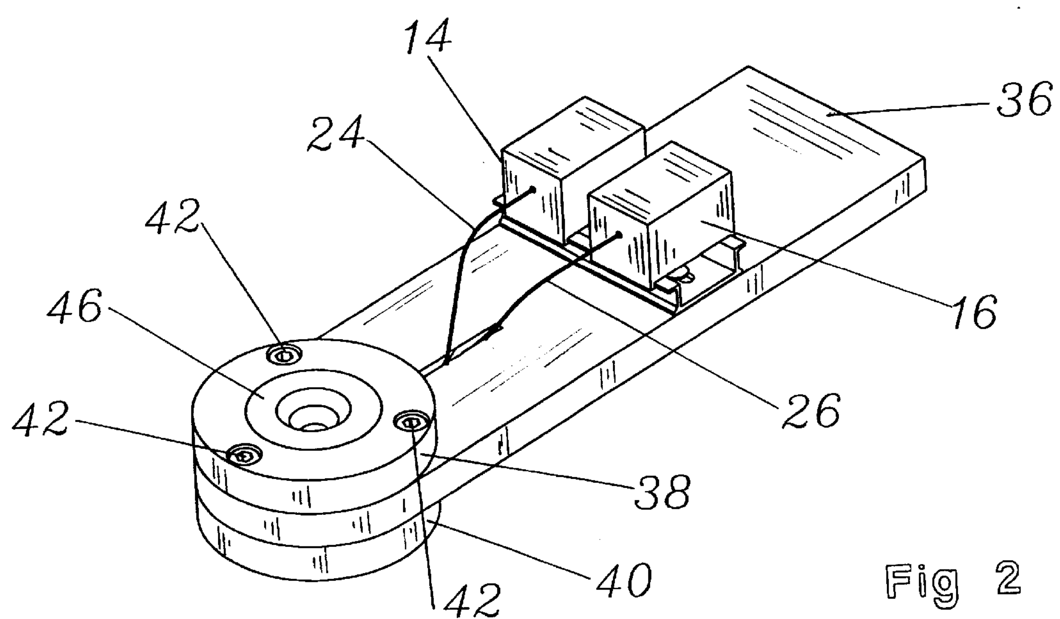
FIG. 2 is an enlarged perspective view of components of the inspection system illustrated in FIG. 1.
Figure 3:
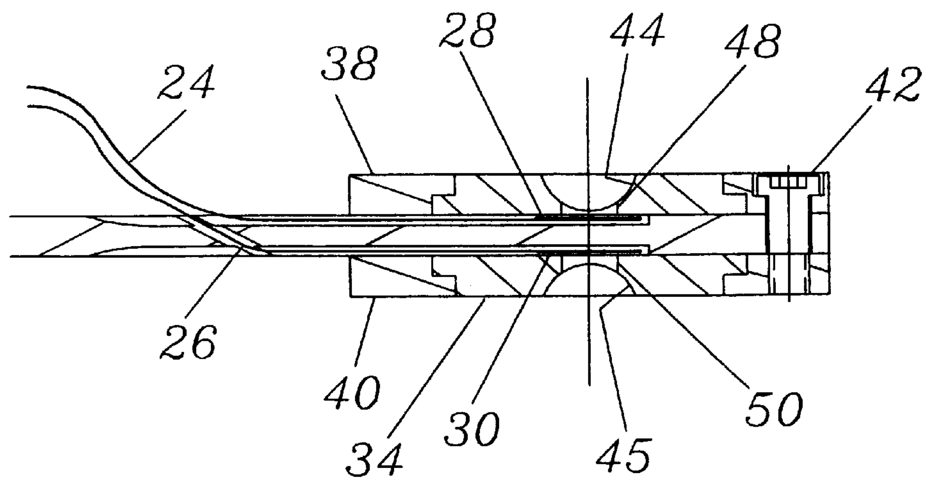
FIG. 3 is a cross-sectional view of a portion of the structure illustrated in FIGS. 1 and 2, taken on the lines 3—3 of FIG. 2.
Figure 4:
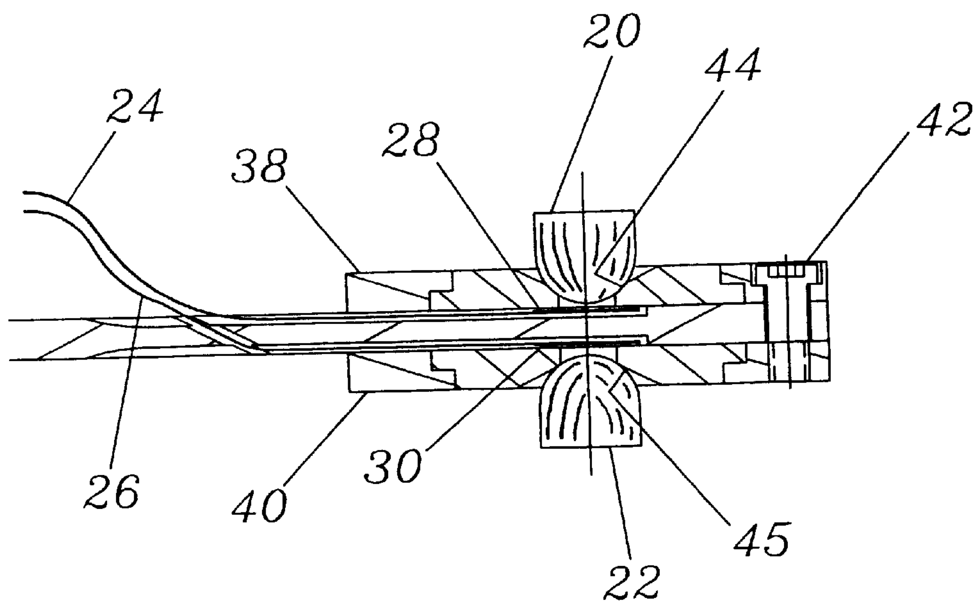
FIG. 4 is an cross-sectional view similar to FIG. 3 and illustrating opposed welding electrode tips inserted therein.

As shown in the drawings, the sensor 12 includes a pair of interchangeable collets 32 and 34 which are mounted on one end portion of an elongate mounting plate 36 and releasably retained thereon through the agency of retainer rings 38 and 40 respectively secured to the mounting plate 36 as by screws such as 42. The mounting plate 36 may be formed of metal or any other suitable material having sufficient strength to withstand the forces exerted thereon. As shown in FIGS. 1 and 2 of the drawings, the other end portion of the mounting plate 36 supports the units 14 and 16.

Figure 5:
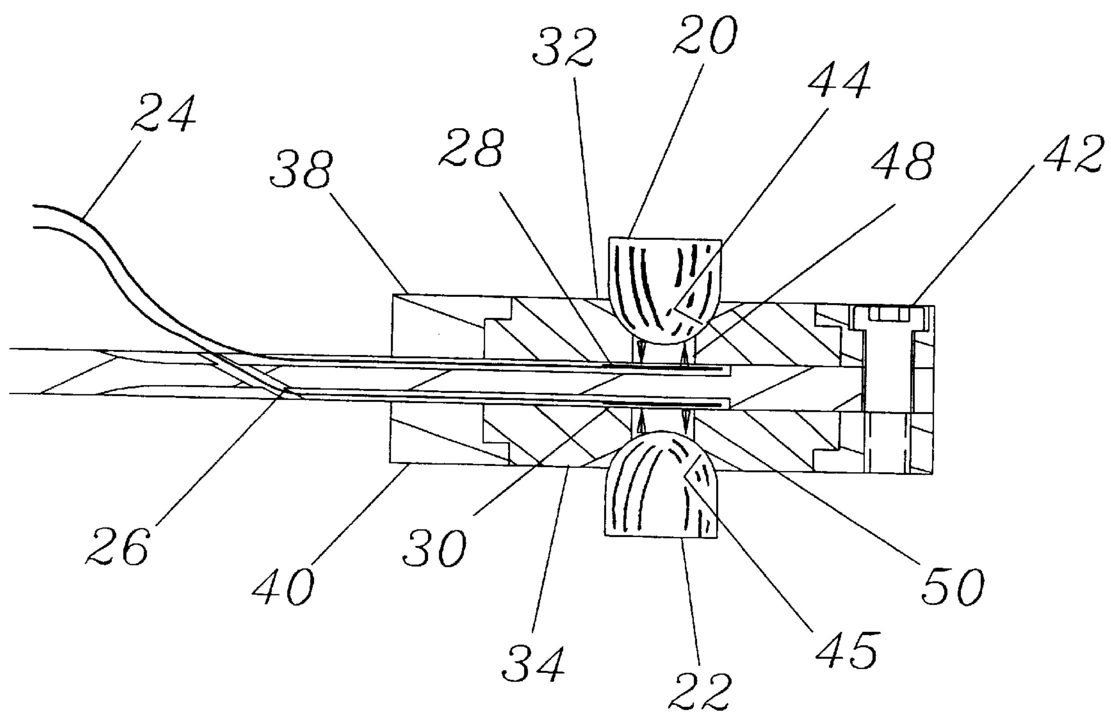
FIG. 5 is an enlarged view of the structure shown in FIG. 4 and illustrating the paths of the emitted light and the reflected light through the collets incorporated in the sensor head.

The collets 32 and 34 define concave cavities 44 and 45 of a configuration that is complementary to the face of the tip of the particular electrode being inspected. It will be understood that there are numerous sizes and shapes of welding electrodes that can be used in resistance welding processes, and the collet cavities 44 and 45 are configured to complement the shape of the electrode being inspected. The collets 32 and 34 are preferably made of hardened steel to resist wear and withstand the forces applied thereto. As shown in FIG. 2, the collets preferably have a taper 46 at the mouth side thereof to assist in aligning the electrodes with the shaped cavity in the collet. As shown in the drawings, the collets 32 and 34 define passageways 48 and 50, respectively, open at each end thereof and through which light beams emitted from the fiber-optic heads 28 and 30, respectively, can pass to the face of the adjacent electrode and be reflected therefrom to the reflective model fiber-optic heads 28 and 30, respectively, as indicated by the arrows in FIG. 5.

As is well known in the art, standard welding electrodes are supplied in different diameters and different tip face shapes, and special shapes are often produced to meet specific requirements. The inspection system embodying the present invention requires that only the collets need to be changed to match the selected electrodes required for any particular welding application. It will be understood that both of the collets may be of the same configuration or different configurations or they may be matched to any combination of electrodes as required for the particular welding operation.

In the operation of the inspection system 10, the sensor 12 is placed between the electrodes 20 and 22 so that the electrodes are disposed in the cavities 44 and 45 defined by the collets 32 and 34. The sensitivity values of the emitted light outputs and the reflected light inputs of the units 14 and 16 are adjusted in a manner well known in the art so that the fiber-optic cable heads 28 and 30 emit light beams of a desired value, which beams past through the passageways 48 and 50, respectively, and impinge on the adjacent surfaces of the electrodes 20 and 22, respectively. The light reflected by such surfaces is then reflected back through the passageways 48 and 50 to the cable heads 28 and 30, respectively, and transmitted back to the units 14 and 16 through the cables 24 and 26. If the electrodes are properly dressed, the amount of reflected light received by the units 14 and 16 will meet predetermined sensitivity values and the units 14 and 16 will verify that the electrodes have been properly dressed. On the other hand, if the amount of reflected light received by the units 14 an 16 is above or below predetermined sensitivity values, the units will not verify that the electrodes have been properly dressed, and the units will sound an alarm and/or shut down the welding operation or otherwise alert the users thereof that the electrodes did not pass inspection. Such rejection may occur, for example, because blackened surfaces of the electrode tips were not removed by the dressing operation with the result that the surfaces were not sufficiently lustrous and glistening to reflect the required amount of light to pass inspection. Such rejection could also occur, for example, because mushroomed electrode tips were not properly dressed and would not fit in the cavities 44 or 45, thereby preventing sufficient light to be reflected therefrom. Also, if an electrode tip was improperly dressed to define a pointed shape, the point would project into the passageways 48 and 50 and consequently reflect too much light thereby exceeding the predetermined sensitivity values of the units 14 and 16.

From the foregoing, it will be appreciated that inspection systems embodying the present invention provide improved means for verifying that resistance welding electrode tips have been properly dressed thereby reducing the risks involved in resistance welding operations and reducing the problems that may be caused by welding with electrodes having tips that were not properly dressed. It will also be appreciated that the present invention provides an improved inspection system incorporating novel fiber-optic sensing means for evaluating welding electrode tip surfaces, physical shape and condition, and the relationship of such tips to predetermined criteria. In addition, the present invention provides an improved inspection system capable of simultaneously inspecting two opposing electrode tips to evaluate the suitability of such tips for continuing welding operations. Moreover, the present invention enables the inspection of welding electrodes of various sizes and shapes merely by changing collets incorporated in the system, and also permits two welding electrodes of different sizes and shapes to be inspected simultaneously. Inspection systems embodying the present invention may be mounted in close proximity to an electrode tip dressing machine or a welding gun, and the entire inspection system is relatively easy to manufacture and assemble at an economical cost and at the same time provides long life and reliability in operation.

While a preferred embodiment of the invention has been illustrated and described, it will be understood that various changes and modifications may be made without departing from the spirit of the invention.

What is claimed is:

1. An inspection system for verifying that a resistance welding electrode has been dressed to predetermined criteria, said system comprising, in combination, light generating means, reflected light sensing means, a sensor defining a cavity for receiving a tip portion of a welding electrode, said sensor defining a passageway open at each end and communicating with said cavity, first fiber-optic means effective to transmit light from said light generating means to said cavity through said passageway, second fiber-optic means effective to transmit light reflected from said cavity through said passageway to said reflected light sensing means, means effective to determine whether the reflected light received by said light sensing means meets predetermined values, and means effective to indicate that the reflected light received by said sensing means does not meet predetermined values.

2. An inspection system for verifying that a resistance welding electrode has been dressed to predetermined criteria, said system comprising, in combination, light generating means, reflected light sensing means, a sensor defining a cavity for receiving a tip portion of a welding electrode, said sensor defining a passageway open at each end and communicating with said cavity, first fiber-optic means effective to transmit light from said light generating means to said cavity through said passageway, second fiber-optic means effective to transmit light reflected from said cavity through said passageway to said reflected light sensing means, means effective to determine whether the reflected light received by said light sensing means meets predetermined values, and collet means defining said cavity and said passageway.

3. An inspection system for verifying that a resistance welding electrode has been dressed to predetermined criteria, said system comprising, in combination, light generating means, reflected light sensing means, a sensor defining a cavity for receiving a tip portion of a welding electrode, said sensor defining a passageway open at each end and communicating with said cavity, first fiber-optic means effective to transmit light from said light generating means to said cavity through said passageway, second fiber-optic means effective to transmit light reflected from said cavity through said passageway to said reflected light sensing means, means effective to determine whether the reflected light received by said light sensing means meets predetermined values, and means for simultaneously inspecting a pair of electrodes.

4. An inspection system for verifying that a resistance welding electrode has been dressed to predetermined criteria, said system comprising, in combination, light generating means, reflected light sensing means, a sensor defining a cavity for receiving a tip portion of a welding electrode, said sensor defining a passageway open at each end and communicating with said cavity, first fiber-optic means effective to transmit light from said light generating means to said cavity through said passageway, second fiber-optic means effective to transmit light reflected from said cavity through said passageway to said reflected light sensing means, means effective to determine whether the reflected light received by said light sensing means meets predetermined values, and means for simultaneously inspecting a pair of electrodes having different tip portion configurations.

5. An inspection system for verifying that a resistance welding electrode has been dressed to predetermined criteria, said system comprising, in combination, light generating means, reflected light sensing means, a sensor defining a cavity for receiving a tip portion of a welding electrode, said sensor defining a passageway open at each end and communicating with said cavity, first fiber-optic means effective to transmit light from said light generating means to said cavity through said passageway, second fiber-optic means effective to transmit light reflected from said cavity through said passageway to said reflected light sensing means, means effective to determine whether the reflected light received by said light sensing means meets predetermined values, and a mounting plate, said mounting plate supporting said sensor and said light generating means and said reflected light sensing means.

6. An inspection system for verifying that a resistance welding electrode has been dressed to predetermined criteria, said system comprising, in combination, light generating means, reflected light sensing means, a sensor defining a cavity for receiving a tip portion of a welding electrode, said sensor defining a passageway open at each end and communicating with said cavity, first fiber-optic means effective to transmit light from said light generating means to said cavity through said passageway, second fiber-optic means effective to transmit light reflected from said cavity through said passageway to said reflected light sensing means, means effective to determine whether the reflected light received by said light sensing means meets predetermined values, said sensor defining multiple cavities each for receiving a tip portion of a welding electrode.

7. An inspection system for verifying that a resistance welding electrode has been dressed to predetermined criteria, said system comprising, in combination, a sensor defining a cavity for receiving a tip portion of an electrode, first fiber-optic means connecting said cavity with a light generating source, second fiber-optic means connecting said cavity with reflected light sensing means, means for determining whether light transmitted from said light generating means to said cavity by said first fiber-optic means and reflected from the surface of an electrode disposed in said cavity and transmitted by said second fiber-optic means to said light sensing means meets predetermined values, and means effective to indicate that the reflected light received by said sensing means does not meet predetermined values.

8. An inspection system for verifying that a resistance welding electrode has been dressed to predetermined criteria, said system comprising, in combination, a sensor defining a cavity for receiving a tip portion of an electrode, first fiber-optic means connecting said cavity with a light generating source, second fiber-optic means connecting said cavity with reflected light sensing means, means for determining whether light transmitted from said light generating means to said cavity by said first fiber-optic means and reflected from the surface of an electrode disposed in said cavity and transmitted by said second fiber-optic means to said light sensing means meets predetermined values, said sensor defining a plurality of cavities each for receiving a tip portion of an electrode, fiber-optic means connecting each of said cavities with a light generating source, additional fiber-optic means connecting said cavities with reflected light sensing means, and means for determining whether light transmitted from said light generating means to each of said cavities and reflected from the surfaces of electrodes disposed in said cavities and transmitted to said light sensing means meets predetermined values.

9. An inspection system for verifying that a resistance welding electrode has been dressed to predetermined criteria, said system comprising, in combination, a sensor defining a cavity for receiving a tip portion of an electrode, first fiber-optic means connecting said cavity with a light generating source, second fiber-optic means connecting said cavity with reflected light sensing means, means for determining whether light transmitted from said light generating means to said cavity by said first fiber-optic means and reflected from the surface of an electrode disposed in said cavity and transmitted by said second fiber-optic means to said light sensing means meets predetermined values, and means for simultaneously inspecting a plurality of electrodes having different tip portion configurations.

10. An inspection system for verifying that a resistance welding electrode has been dressed to predetermined criteria, said system comprising, in combination, a sensor defining a cavity for receiving a tip portion of an electrode, first fiber-optic means connecting said cavity with a light generating source, second fiber-optic means connecting said cavity with reflected light sensing means, means for determining whether light transmitted from said light generating means to said cavity by said first fiber-optic means and reflected from the surface of an electrode disposed in said cavity and transmitted by said second fiber-optic means to said light sensing means meets predetermined values, and a mounting plate, said mounting plate supporting said sensor and said light generating means and said reflected light sensing means.

11. An inspection system for verifying that a resistance welding electrode has been dressed to predetermined criteria, said system comprising, in combination, a sensor defining a cavity for receiving a tip portion of an electrode, first fiber-optic means connecting said cavity with a light generating source, second fiber-optic means connecting said cavity with reflected light sensing means, means for determining whether light transmitted from said light generating means to said cavity by said first fiber-optic means and reflected from the surface of an electrode disposed in said cavity and transmitted by said second fiber-optic means to said light sensing means meets predetermined values, said sensor defining multiple cavities each for receiving a tip portion of a welding electrode.

12. An inspection system for verifying that a resistance welding electrode has been dressed to predetermined criteria, said system comprising, in combination, a mounting plate, a sensor carried by said mounting plate, said sensor including a collet defining a cavity for receiving a tip portion of an electrode, a light generating unit carried by said mounting plate, a reflected light sensing unit carried by said mounting plate, fiber-optic means connecting said cavity with said light generating unit and said reflected light sensing unit, and means carried by said mounting plate and effective to determine whether the reflected light received by said light sensing unit meets predetermined criteria.

* * * * *